United States Patent
Luo et al.

(10) Patent No.: US 11,517,386 B2
(45) Date of Patent: Dec. 6, 2022

(54) DUAL-USE HANDLE

(71) Applicants: SHANGHAI REACH MEDICAL INSTRUMENT CO., LTD., Shanghai (CN); THE FOURTH MILITARY MEDICAL UNIVERSITY OF THE CHINESE PEOPLE'S LIBERATION ARMY, Xi'an (CN)

(72) Inventors: Zhuojing Luo, Xi'an (CN); Xiaomin Huang, Shanghai (CN)

(73) Assignees: SHANGHAI REACH MEDICAL INSTRUMENT CO., LTD., Shanghai (CN); THE FOURTH MILITARY MEDICAL UNIVERSITY OF THE CHINESE PEOPLE'S LIBERATION ARMY, Xian (CN)

( * ) Notice: Subject to any disclaimer, the term of this patent is extended or adjusted under 35 U.S.C. 154(b) by 433 days.

(21) Appl. No.: 16/628,261

(22) PCT Filed: Aug. 14, 2018

(86) PCT No.: PCT/CN2018/100316
§ 371 (c)(1),
(2) Date: Jan. 3, 2020

(87) PCT Pub. No.: WO2019/134366
PCT Pub. Date: Jul. 11, 2019

(65) Prior Publication Data
US 2020/0214781 A1    Jul. 9, 2020

(30) Foreign Application Priority Data
Jan. 5, 2018    (CN) .......................... 201810013119.0

(51) Int. Cl.
*B25B 23/16*    (2006.01)
*A61B 50/20*    (2016.01)
(Continued)

(52) U.S. Cl.
CPC .............. *A61B 50/20* (2016.02); *B25B 15/02* (2013.01); *B25B 23/16* (2013.01); *B25G 1/005* (2013.01);
(Continued)

(58) Field of Classification Search
CPC .......... B25G 1/06; B25G 1/063; B25G 1/066; B25G 1/005; B25G 3/06; B25G 3/18;
(Continued)

(56) References Cited

U.S. PATENT DOCUMENTS 2,950,746 A  *  8/1960  Towne  .................... B25B 15/04
                                                      81/177.1
3,752,202 A  *  8/1973  Condon  ................. B25G 1/043
                                                      81/177.85
(Continued)

FOREIGN PATENT DOCUMENTS

CN    103817661    5/2014
CN    102507069    6/2016
(Continued)

OTHER PUBLICATIONS

International Search Report in PCT/CN2018/100316, issued by ISA, dated Nov. 7, 2019.
Written Opinion of the International Search Report in PCT/CN2018/100316, issued by ISA, dated Nov. 7, 2019.

*Primary Examiner* — Scott A Smith
(74) *Attorney, Agent, or Firm* — Zhu Lehnhoff LLP

(57) ABSTRACT

The invention provides a dual-purpose handle, comprising a body, wherein mounting holes are provided in the body and are used for connecting to functional members; the mounting holes are provided in the body in both an axial direction and a radial direction; axial and radial mounting holes provided in the body can enable the handle and the functional members to easily and quickly switch between two connection forms, i.e. straight and T-shaped; and torsional
(Continued)

torques that are different in magnitude can be output by means of different connection manners under the action of the same operation force. Clamping devices fitted with the functional members are arranged in the mounting holes; and when the functional members are connected to the handle, the clamping devices can fix the functional members and prevent same from rotating in a cavity of the body of the handle. The axial and radial holes of the handle are configured to be through holes, so that the handle can be adapted to guide needles of different sizes passing through same and is suitable for minimally invasive surgery, thereby further expanding the range of use of the handle.

13 Claims, 3 Drawing Sheets

(51) Int. Cl.
| | | |
|---|---|---|
| *B25B 15/02* | (2006.01) | |
| *B25G 3/06* | (2006.01) | |
| *B25G 1/00* | (2006.01) | |
| *A61B 90/00* | (2016.01) | |
| *A61B 17/00* | (2006.01) | |
| *B27F 1/02* | (2006.01) | |
| *B25B 23/00* | (2006.01) | |

(52) U.S. Cl.
CPC ...... *B25G 3/06* (2013.01); *A61B 2017/00464* (2013.01); *A61B 2090/064* (2016.02); *B25B 23/0035* (2013.01); *B27F 1/02* (2013.01)

(58) Field of Classification Search
CPC ..... B25B 23/0035; B25B 23/14; B25B 23/16; B25B 15/02; B25B 15/00; B25F 1/02
USPC ........... 81/177.1, 177.2, 177.4, 177.5, 177.8, 81/177.85, 438, 439, 479; 16/110.1, 422; 173/2, 176, 29, 170, 171
See application file for complete search history.

(56) References Cited

U.S. PATENT DOCUMENTS

| | | | | |
|---|---|---|---|---|
| 4,056,020 A * | 11/1977 | Coviello | ................ | B25B 15/00 |
| | | | | 81/177.85 |
| 4,787,276 A * | 11/1988 | Condon | ................ | B25G 1/066 |
| | | | | 81/177.1 |
| 4,996,896 A * | 3/1991 | Bachand | ................ | B25G 1/066 |
| | | | | 81/450 |
| 5,477,758 A * | 12/1995 | Cunningham | ........ | F16H 7/1281 |
| | | | | 81/177.85 |
| 5,544,379 A | 8/1996 | Chen | | |
| 5,743,737 A * | 4/1998 | Hawn | ................. | A61C 8/0089 |
| | | | | 81/177.8 |
| 6,378,402 B1 * | 4/2002 | Kalomeris | ............ | B25G 1/005 |
| | | | | 81/177.4 |
| 6,606,925 B1 * | 8/2003 | Gmeilbauer | ............ | B25B 23/16 |
| | | | | 81/439 |
| 6,922,870 B2 * | 8/2005 | Tontz, Sr. | ............. | B25G 1/066 |
| | | | | 81/177.4 |
| 7,287,450 B1 * | 10/2007 | Liao | ........................ | B25B 15/02 |
| | | | | 81/177.9 |
| 8,051,748 B2 * | 11/2011 | Lin | ........................ | B25B 15/00 |
| | | | | 81/177.1 |
| 8,096,213 B2 * | 1/2012 | Miers | ................. | B25B 23/0035 |
| | | | | 81/439 |
| 2004/0250378 A1 * | 12/2004 | Tontz, Sr. | ............. | B25G 1/066 |
| | | | | 16/110.1 |
| 2009/0126538 A1 * | 5/2009 | Miers | ........................ | B25F 1/02 |
| | | | | 81/177.85 |
| 2009/0288526 A1 * | 11/2009 | Hsieh | ..................... | B25B 13/04 |
| | | | | 81/479 |
| 2016/0129569 A1 * | 5/2016 | Lehnert | ................. | G08C 17/02 |
| | | | | 340/12.54 |

FOREIGN PATENT DOCUMENTS

| | | |
|---|---|---|
| CN | 205325538 | 6/2016 |
| CN | 206216564 | 6/2017 |
| CN | 108210081 | 6/2018 |

* cited by examiner

DUAL-USE HANDLE

TECHNICAL FIELD

The invention relates to the technical field of orthopedic medical devices and tools, in particular to a dual-purpose handle.

BACKGROUND

In medical operation, various forceps and threaded rod devices are required for assisting people in performing operations successfully, while the application of the forceps and rod devices needs assistance of handles. At present, handles used in the clinic are poor in interchangeability and single in functions; in this way, the types of the handles in a single operation are various, and the number is increased; the labor cost and the device acquisition cost are increased greatly, and moreover the acting force applied to the devices by hand are not liable to control; the adjustable range is small, and consequently the risk of damage to skeletons and relevant devices is increased.

SUMMARY OF THE INVENTION

The invention aims to provide a dual-purpose handle with the simple structure and easy operation, and the requirement of straight connection or T type connection between the dual-purpose handle and functional parts can be met.

In order to solve the above problems, the invention relates to a dual-purpose handle, comprising a body, and mounting holes are arranged in the body, and used to connect the functional parts. The mounting holes are arranged in the body axially and radially.

The mounting holes arranged in the body axially and radially enable the connection between the handle and the functional parts to switch between a straight type and a T type conveniently and efficiently. Different connection modes can output different torsional moments under the effect of the same operating force so that the control range is expanded.

As the further improvement of the invention, clamping stop devices which are fit with the functional parts are arranged in the mounting holes.

The clamping stop devices are arranged in the mounting holes. When the functional parts are connected with the handle, the functional parts can be fixed through the clamping stop devices axially, and prevented from being rotated in the body 1 cavity of the handle.

As the further improvement of the invention, the clamping stop devices are arranged as protrusions corresponding to grooves of the functional parts.

As the further improvement of the invention, the protrusions are elastomers.

When the functional parts are inserted and connected along the body cavity of the handle, the elastic protrusions arranged on the handle can locate the functional parts automatically. On the other hand, through pulling of the elastic protrusions arranged on the handle, the functional parts can be disengaged along the body cavity of the handle conveniently.

As the further improvement of the invention, the free ends of the protrusions are in smooth arc transition.

The smooth arc transition of the free ends of the protrusions enables the protrusions to slide in or out from grooves of the functional parts matched with the protrusions more smoothly.

As the further improvement of the invention, the protrusions and the body are arranged integrally and are in seamless connection.

Through the protrusions arranged with the body integrally, the handle has the advantages of low manufacturing cost, firm combination, long service life and the like.

As the further improvement of the invention, the mounting holes are arranged as through holes.

The axial hole and the radial hole of the handle are arranged as through holes; in this way, the handle is applicable for guide pins in different sizes to penetrate, and the handle is suitable for minimally invasive surgery; the application range of the handle is further expanded.

As the further improvement of the invention, anti-slip grooves or anti-slip protrusions are arranged on the body.

The anti-slip grooves or the anti-slip protrusions arranged on the body enable operating personnel to hold the handle in the using process more securely, and apply the acting force more conveniently.

As the further improvement of the invention, the body is made of ixef 1022 plastic.

As the further improvement of the invention, a strain gauge torque sensor is pasted on the surface of the body.

The strain gauge torque sensor is pasted on the surface of the body, and can be used to measure the torque applied to the functional parts by the operating personnel in real time; in this way, the risk is reduced greatly.

BRIEF DESCRIPTION OF THE DRAWINGS

In order to describe the embodiments of the invention or the technical scheme in the prior art more clearly, a brief introduction to the drawings required to use in the embodiment or the description of the prior art is made below, and obviously the drawings in the following description are only some embodiments of the invention; for those skilled in the art, on the premise that no creative work is done, other drawings can be further obtained according to these drawings.

1—body; 11—mounting hole; 111—axial mounting hole; 112—radial mounting hole; 2—clamping stop device; 21—radial clamping stop device; 22—axial clamping stop device; 3—functional part; 4—groove.

DETAILED DESCRIPTION OF THE PREFERRED EMBODIMENTS

Figure 1:
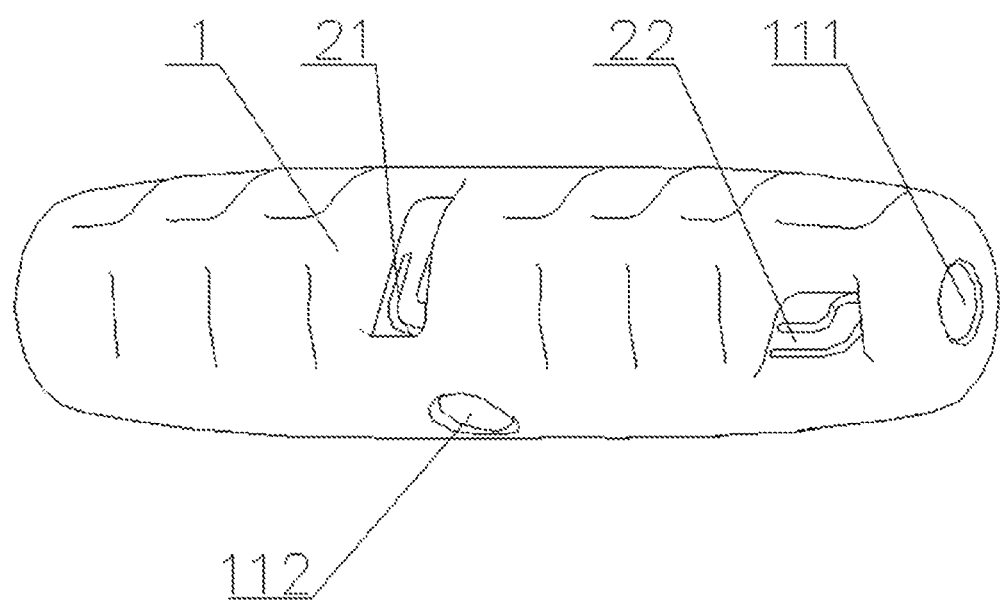
FIG. 1 is a structure diagram of the dual-purpose handle.

A detailed description of the dual-purpose handle of the invention is given below in combination with the embodiments of the invention:

In order to achieve the purposes of the invention, FIG. 1 shows a structure diagram of the dual-purpose handle. The body 1 of the dual-purpose handle is made of ixef 1022 plastic. The anti-slip grooves or the anti-slip protrusions arranged on the body enable operating personnel to hold the handle in the using process more securely, and apply the acting force more conveniently. A radial mounting hole 112 and an axial mounting hole 111 are arranged in the body 1 of the dual-purpose handle radially and axially. The mounting holes are arranged as ¼-inch international common holes so as to expand the application range of the handle as far as possible, and the types and number of the handle are reduced as far as possible. The functional parts 3 are connected with the body 1 through the above mounting holes (111 and 112). In addition, in order to enable the functional parts 3 to connect with the body 1 conveniently, quickly and reliably, the radial clamping stop device 21 and the axial clamping stop device 22 are arranged on the body 1 of the dual-purpose handle radially and axially. The clamping stop devices 21 and 22 are preferably designed as protrusions corresponding to grooves 4 of the functional parts, and can also be arranged in other forms meeting the clamping stop function. The protrusions arranged on the handle are elastomers, and the free ends of the elastomers are in smooth arc transition. When the functional parts 3 are inserted and connected along the body 1 cavity of the handle, the elastomers can locate the functional parts automatically; through pulling of the elastic protrusions arranged on the handle, the functional parts 3 can be disengaged along the body 1 cavity of the handle conveniently. The smooth arc transition of the free ends of the protrusions enables the protrusions to slide in or out from the grooves 4 of the functional parts matched with the protrusions more smoothly. Certainly, in order to reduce the manufacturing cost, enable the protrusions to combine more securely and the service life to prolong, the protrusions and the body can be arranged integrally.

Figure 2:
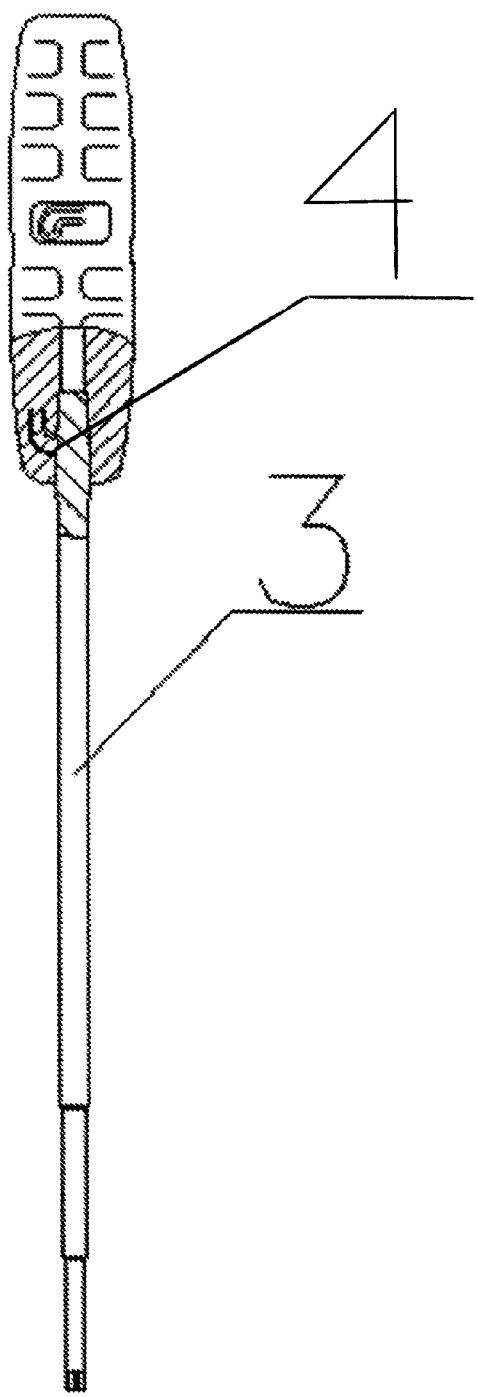
FIG. 2 is a diagram of a usage mode of the dual-purpose handle in the first embodiment of the invention.
Figure 3:
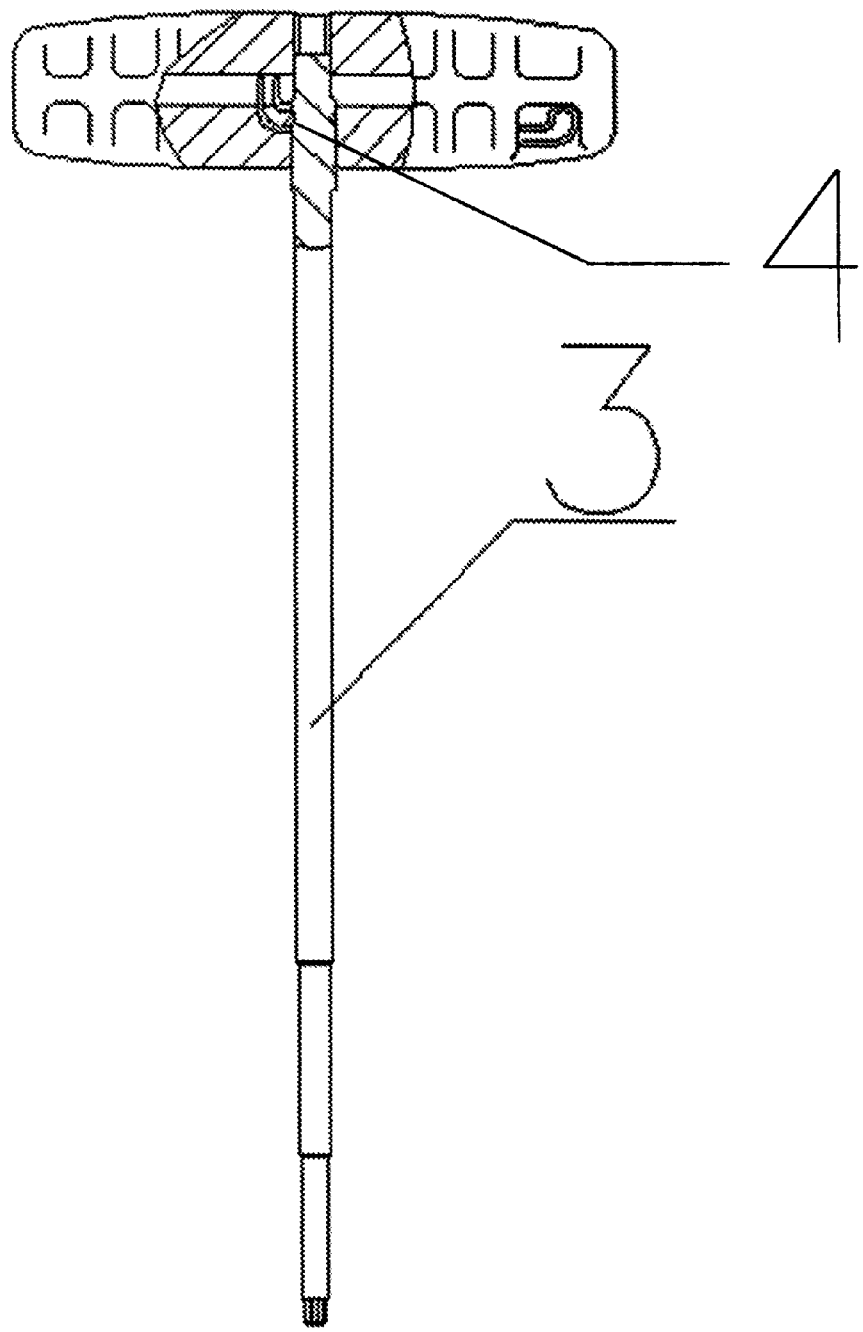
FIG. 3 is a diagram of a usage mode of the dual-purpose handle in the second embodiment of the invention.

FIG. 2 shows a diagram of a usage mode of the dual-purpose handle in the first embodiment of the invention. The functional parts 3 are in straight connection with the body through the axial mounting hole 111 on the body 1; FIG. 3 shows a diagram of a usage mode of the dual-purpose handle in the second embodiment of the invention. The functional parts 3 are in T-type connection with the body through the radial mounting hole 112 on the body 1. The arms of the acting forces are different in the above two connection modes are different so that the controllable range of the torque is expanded. The straight connection can achieve small torque, while the T type connection is used to achieve large torque; in this way, the operability of the handle in the using process is improved. As the further improvement, the strain gauge torque sensor is pasted on the surface of the body, and shows data on a display screen in time so as to measure the torque applied to the functional parts by the operating personnel in real time; in this way, the operating process is more accurate and effective, and the risk is reduced greatly.

As the further improvement, the axial hole and the radial hole of the handle are arranged as through holes; in this way, the handle the handle can be suitable for minimally invasive surgery, and is applicable for guide pins to penetrate; the application range of the handle is further expanded.

The above description of the disclosed embodiments enables those skilled in the art to achieve or use the dual-purpose handle. Different kinds of modifications for these embodiments are apparent to those skilled in the art, and general principles defined in this paper can be achieved in other embodiments without separating from the spirit or range of the invention. Thus, the invention is not limited to the embodiments shown in this paper, but needs to meet the widest range which is consistent with the principles and novel features disclosed in this paper.

The invention claimed is:

1. A dual-purpose handle for holding functional parts comprising:
   a body capable of being grasped by a user of the handle and having first and second lengthwise ends and an outer peripheral surface extending between the lengthwise ends;
   a first mounting hole formed in the body and extending in an axial direction of the body and opening onto one of the lengthwise ends of the body;
   a second mounting hole formed in the body and extending in a radial direction of the body and opening onto the outer peripheral surface of the body;
   a first cavity and a second cavity both formed in the outer peripheral surface of the body;
   a first elastically deformable clamping stop device disposed in the first cavity and having a fixed end rigidly secured to the body within the first cavity and a free end extending from the first cavity into the first mounting hole through a peripheral wall of the first mounting hole; and
   a second elastically deformable clamping stop device disposed in the second cavity and having a fixed end secured to the body within the second cavity and a free end extending from the second cavity into the second mounting hole through a peripheral wall of the second mounting hole,
   wherein when a functional part is inserted into either the first or the second mounting hole, the free end of the first clamping stop device or the second clamping stop device, respectively, can engage with the functional part to fix the functional part against movement in an axial direction of the functional part.

2. A dual-purpose handle as claimed in claim 1 wherein engagement between the free end of one of the clamping stop devices and the functional part when the functional part is inserted into one of the mounting holes prevents rotation of the functional part with respect to the handle.

3. A dual-purpose handle as claimed in claim 2 wherein each of the mounting holes has a circular transverse cross section.

4. A dual-purpose handle as claimed in claim 1 wherein each of the clamping stop devices includes first and second legs each having a first end secured to the body and a second end, and an arcuate transition portion which connects the second ends of the legs to each other and extends into one of the mounting holes for engagement with one of the functional parts.

5. A dual-purpose handle as claimed in claim 1 wherein each of the clamping stop devices is integral with the body of the handle.

6. A dual-purpose handle as claimed in claim 1 wherein each of the clamping stop devices is made of an elastomer.

7. A dual-purpose handle as claimed in claim 1 wherein the body is made of Ixef 1022 plastic.

8. A dual-purpose handle as claimed in claim 1 wherein each of the mounting holes is a through hole having first and second ends which open onto an exterior surface of the body.

9. A dual-purpose handle as claimed in claim 1 wherein the body has anti-slip portions selected from anti-slip grooves and anti-slip protrusions formed on its exterior.

10. A handle arrangement for orthopedic medical procedures comprising:
    a dual-purpose handle as claimed in claim 1;
    a functional part for an orthopedic medical procedure disposed in one of the first and second mounting holes of the handle and having a groove engaging the free end of one of the clamping stop devices to resist movement of the functional part with respect to the handle in an axial direction of the functional part.

11. A handle arrangement as claimed in claim 10 wherein engagement between the free end of the one of the clamping stop devices and the functional part prevents rotation of the functional part with respect to the handle.

12. A dual-purpose handle as claimed in claim 11 wherein each of the mounting holes has a circular transverse cross section.

13. A handle arrangement as claimed in claim 10 wherein the functional part comprises a guide pin for orthopedic medical procedures.

\* \* \* \* \*